US008632461B2

(12) United States Patent
Glossop (10) Patent No.: US 8,632,461 B2
(45) Date of Patent: Jan. 21, 2014

(54) SYSTEM, METHOD AND APPARATUS FOR NAVIGATED THERAPY AND DIAGNOSIS (75) Inventor: Neil David Glossop, Toronto (CA)

(73) Assignee: Koninklijke Philips N.V., Eindhoven (NL)

(*) Notice: Subject to any disclaimer, the term of this patent is extended or adjusted under 35 U.S.C. 154(b) by 1500 days.

(21) Appl. No.: 11/471,604

(22) Filed: Jun. 21, 2006

(65) Prior Publication Data
US 2007/0032723 A1 Feb. 8, 2007

Related U.S. Application Data (60) Provisional application No. 60/692,272, filed on Jun. 21, 2005.

(51) Int. Cl.
A61B 17/00 (2006.01)
A61B 1/00 (2006.01)
A61B 5/05 (2006.01)

(52) U.S. Cl.
USPC .............................. 600/205; 600/103; 600/424

(58) Field of Classification Search
USPC .......... 606/1, 52, 130, 51; 600/103, 104, 114, 600/424, 115–117, 128, 130
See application file for complete search history.

(56) References Cited

U.S. PATENT DOCUMENTS

| 3,021,842 | A | 2/1962 | Flood |
| 4,080,706 | A | 3/1978 | Heilman et al. ................. 29/173 |
| 4,279,252 | A | 7/1981 | Martin ........................ 128/349 R |
| 4,697,595 | A | 10/1987 | Breyer et al. ................. 128/660 |
| 4,722,056 | A | 1/1988 | Roberts et al. ................. 364/413 |
| 4,777,951 | A | 10/1988 | Cribier et al. ................. 128/344 |
| 4,887,606 | A | 12/1989 | Yock et al. ................ 128/662.05 |
| 4,895,168 | A | 1/1990 | Machek ......................... 128/772 |
| 4,935,019 | A | 6/1990 | Papp, Jr. ........................ 604/362 |
| 4,961,433 | A | 10/1990 | Christian ....................... 128/772 |

(Continued)

FOREIGN PATENT DOCUMENTS

| AU | 6367896 | 2/1997 |
| AU | 722539 | 8/2000 |

(Continued)

OTHER PUBLICATIONS

TRA024—Knaan, Dotan, et al., Effective Intensity-Based 2D/3D Rigid Registration Between Fluoroscopic X-Ray and CT, *MICCAI*, vol. 1, 2003, pp. 351-358.

(Continued)

Primary Examiner — Anhtuan T Nguyen
Assistant Examiner — Ryan Henderson (57) ABSTRACT The invention provides an image-guided medical instrument that utilizes a tracking device to track the location of at least a portion of the instrument on at least one image of a patient's anatomy. The instrument may include a handle having an operating element, an elongated flexible body member connected to the handle, wherein the body member includes a lumen, a transmission element housed within the lumen of the body member, and a treatment apparatus connected to end of the transmission element, wherein actuation of the operating element actuates the treatment apparatus via the transmission element. The body member also includes at least one sensor element that is utilized by the tracking device to determine position information regarding the treatment apparatus that is used to display the location of the treatment apparatus on the at least one image of the patient's anatomy.

16 Claims, 8 Drawing Sheets

(56) References Cited

U.S. PATENT DOCUMENTS

| | | | | |
|---|---|---|---|---|
| 5,014,708 A * | 5/1991 | Hayashi et al. | 600/117 |
| 5,042,486 A | 8/1991 | Pfeiler et al. | 128/653 R |
| 5,045,080 A | 9/1991 | Dyer et al. | 604/362 |
| 5,085,659 A | 2/1992 | Rydell | 606/47 |
| 5,116,345 A | 5/1992 | Jewell et al. | 606/130 |
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.2 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A * | 2/1995 | Owens et al. | 600/424 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,437,277 A | 8/1995 | Dumoulin et al. | 128/653.1 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,480,382 A * | 1/1996 | Hammerslag et al. | 600/585 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A | 11/2000 | Osadchy et al. | 324/67 |
| 6,165,184 A * | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 | 4/2002 | Hunter et al. | 600/407 |
| 6,383,174 B1 * | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 600/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,127 B1 | 7/2003 | McKinnon | 600/411 |
| 6,591,129 B1 | 7/2003 | Ben-Haim et al. | 600/424 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,719,700 B1 | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 * | 5/2005 | Rahn et al. | 600/429 |
| 6,916,290 B2 | 7/2005 | Hedengren et al. | 600/549 |
| 7,085,400 B1 | 8/2006 | Holsing et al. | 382/103 |
| 7,386,339 B2 * | 6/2008 | Strommer et al. | 600/424 |
| 7,570,791 B2 | 8/2009 | Frank et al. | 382/132 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |

(56) References Cited

U.S. PATENT DOCUMENTS

| | | | |
|---|---|---|---|
| 2001/0038354 A1 | 11/2001 | Gilboa | 342/450 |
| 2001/0039419 A1* | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/509 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0087101 A1 | 7/2002 | Barrick et al. | 600/587 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1* | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1* | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/429 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1* | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1* | 11/2004 | Miller | 128/207.14 |
| 2004/0234933 A1 | 11/2004 | Dawson et al. | 434/262 |
| 2004/0249267 A1 | 12/2004 | Gilboa | |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1* | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1* | 4/2005 | Glossop | 604/529 |
| 2005/0107688 A1 | 5/2005 | Strommer | 600/424 |
| 2005/0182295 A1 | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| BR | 9609484 | 12/1999 |
| CA | 2226938 | 2/1997 |
| DE | 69420228 D | 9/1999 |
| DE | 69420228 T | 4/2000 |
| DE | 19845267 | 5/2000 |
| EP | 0 845 959 | 6/1998 |
| EP | 0 654 244 | 8/1999 |
| EP | 1466552 | 10/2004 |
| IL | 0107523 | 1/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 | 12/1998 |
| WO | WO 00/22904 | 4/2000 |

OTHER PUBLICATIONS

TRA025 —Gee, A. H., et al., "3D Ultrasound Probe Calibration Without a Position Sensor", CUED/F-INFENG/TR 488, University of Cambridge, Department of Engineering, Sep. 2004, 21 pages.

TRA026—Lindseth, Frank, et al., "Probe Calibration for Freehand 3D Ultrasound Reconstruction and Surgical Navigation", Dec. 2002, 27 pages.

TRA027—Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

TRA028—Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

TRA001—Tanase, Dafina, et al., "Magnetic Sensors for Use on Guide Wires or Catheters", in *SeSens* 2001, in press 2002, pp. 868-872.

TRA002—Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

TRA003—Solomon, Stephen B., et al., "Real-Time Cardiac Catheter Navigation on Three-Dimensional CT Images", *Journal of Interventional Cardiac Electrophysiology*, vol. 8, 2003, pp. 27-36.

TRA004—Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

TRA005—Baert, Shirley A. M., et al., "Endpoint Localization in Guide Wire Tracking During Endovascular Interventions", *Academic Radiology*, vol. 10, No. 12, Dec. 2003, pp. 1424-1432.

TRA006—Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

TRA007—Baert, Shirley A. M., et al., "Guide-Wire Tracking During Endovascular Interventions", *IEEE Transactions on Medical Imaging*, vol. 22, No. 8, Aug. 2003, pp. 965-972.

TRA008—Kobashi, Keiji, et al., "A New Biomechanical Model Based Approach on Brain Shift Compensation", *MICCAI 2003*, LNCS 2878, 2003, pp. 59-66.

TRA009—Timinger, Holger, et al., "Motion Compensation for Interventional Navigation on 3D Static Roadmaps Based on an Affine Model and Gating", *Physics in Medicine and Biology*, vol. 49, 2004, pp. 719-732.

TRA010—Lorigo, Liana M., et al., "Curves: Curve Evolution for Vessel Segmentation", *Medical Image Analysis*, vol. 5, 2001, pp. 195-206 (pp. 1-14).

TRA011—Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.

TRA012—Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

(56) References Cited

OTHER PUBLICATIONS

TRA013—"Semi-Automatic Registration for Image Guided Surgery", Traxtal poster presented at CAOS '99 (Computer Assisted Orthopaedic Surgery, 4$^{th}$ International Symposium), MICCAI, Mar. 17-19, 1999, Davos, Switzerland, 1 page.

TRA014—Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Spring-Verlag Heidelberg, 2003, pp. 215-222.

TRA015—Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

TRA016—SuperDimension, Ltd, web page, updated in Sep. 2005, 1 page.

TRA017—Schweikard, Achim, et al., "Robotic Motion Compensation for Respiratory Movement During Radiosurgery", *Computer Aided Surgery*, vol. 5, 2000, pp. 263-277.

TRA018—Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

TRA019—Ellsmere, James, et al., "A Navigation System for Augmenting Laparoscopic Ultrasound", Center for Integration of Medicine and Innovative Technology, Cambridge, Massachusetts, 8 pages.

TRA020—Hofstetter, R., et al., "Fluoroscopy Based Surgical Navigation—Concept and Clinical Applications", Maurice E. Muller Institute for Biomechanics, University of Bern, Switzerland, 1997, 3 pages.

TRA021—Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

TRA022—Summers, Ronald M., et al., "Colonic Polyps: Complementary Role of Computer-Aided Detection in CT Colonography", *Radiology*, vol. 225, No. 2, Nov. 2002, pp. 391-399.

TRA023—Hara, A. K., et al., "Reducing Data Size and Radiation Dose for CT Colonography", *AJR*, vol. 168, May 1997, pp. 1181-1184.

TRA029—RITA StarBurst Soft Tissue Access System and RITA StarBurst Hard Tissue Access System, http://www.ritamedical.com, Rita Medical Systems, Inc., copyright 2002, 8 pages.

TRA030—Cool-tip RF Tissue Ablation System, Cool-tip RF System, and Cool-tip Electrodes, http://www.valleylab.com/static/cooltip/products.html, Valleylab, copyright 2004, 4 pages.

TRA031—LeVeen Needle Electrode, Boston Scientific, printed from http://www.bostonscientific.com/med_specialty/deviceDetail.jhtml?task=tskBasicDevice . . . , printed on Sep. 13, 2004, 1 page.

TRA032—Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

* cited by examiner

SYSTEM, METHOD AND APPARATUS FOR NAVIGATED THERAPY AND DIAGNOSIS

RELATED APPLICATIONS

This application claims priority to U.S. Provisional Application No. 60/692,272, filed Jun. 21, 2005, which is hereby incorporated by reference herein in its entirety.

FIELD OF THE INVENTION

The invention relates to a system, method and apparatus for navigated therapy and diagnosis.

BACKGROUND OF THE INVENTION

Access to natural and artificial passages in the body for treatment or investigation for possible treatment traditionally make use of elongated instruments that are inserted into the body. These instruments can be inserted into the body alone (e.g., as in a biopsy needle) or may make use of other implements such as an endoscope (e.g., a bronchoscope or colonoscope) through which the elongated instruments are inserted. Typical devices for access to natural or artificial passages in the body may include, for example, spring loaded biopsy "guns," endoscopic biopsy forceps, biopsy needles, polypectomy snares, cytology brushes, biliary guidewires, sphincterotomes, endoscopic retrograde cholangiography (ERCP) catheters, stone retrieval balloons, stents, lithotripsy baskets, graspers, baskets, rat-tooth and alligator forceps, sclerotherapy/injection needles, bipolar coagulation probes, dilation balloons, radiofrequency ablation devices, microwave ablation devices, cryotherapy probes, or other devices.

Many of these devices have a mechanical or electrical component located near the tip to perform some actuation of a treatment apparatus such as, for example, movement of a set of biopsy jaws or grasper, delivery of energy, actuation of a biopsy mechanism, or other actuation. Directing the tip of these devices into locations of interest, such as those identified preoperatively or intraoperatively through medical scans of the patient (such as CT, MR, PET, SPECT, x-ray etc.) can be difficult. This is especially true if, among other things, the location of the instrument relative to a lesion or other area of interest cannot be visualized directly. If the tip of an instrument is not properly positioned, multiple problems can arise such as, for example, iatrogenic damage to tissue can be imparted, samples of tissue can be obtained that are not the intended target of the procedure, or other problems.

Sometimes, the location of a target lesion or other area of interest is known on a preoperative scan but insufficient landmarks are identifiable during the actual surgical intervention to easily locate the lesion or area of interest. This is especially true if the lesion or area of interest does not appear distinctly different from surrounding tissues under readily available intraoperative imaging modalities. These intraoperative imaging modalities may include x-rays, optical examination or ultrasound. When used, the lesion, area of interest, and/or instrument may be invisible or inaccessible to the "live" (i.e., intraoperative) imaging modality, may appear in insufficient resolution, or the image of the lesion might be degraded through the presence of intervening anatomy. This may render it difficult or impossible to determine the location of the instrument relative to the lesion or area of interest using traditional intraoperative imaging. Furthermore, some imaging modalities, such as those that are based on x-rays, may impart ionizing radiation or be otherwise harmful to patient and surgeon. Even when the intraoperative imaging modalities are able to render a lesion or area of interest and instrument, the images produced can sometimes be difficult to interpret or can take excessive time to obtain. Furthermore, the imaging modalities used for the initial preoperative scans may be inappropriate or otherwise unavailable for use intraoperatively (i.e., during the actual interventional procedure).

For these and other reasons, it is desirable to construct systems, devices and methods for performing interventions where an instrument's tip location can be tracked while inside the patient and a representation of the instrument can be displayed on preoperative or intra-operative scans in which the salient anatomy is visible. It is further desirable that such systems, devices, and methods are usable with flexible instruments to perform the intervention, and that these instruments perform and function similarly to conventional instruments. It is further desirable to use such methods to track instruments that contain a therapy or tissue sampling component at the tip. It is further desirable that these operate in both soft and hard tissue.

SUMMARY OF THE INVENTION

In one embodiment, the invention provides an image-guided medical instrument, which can be used in minimally invasive surgery. An example of an instrument of the invention may include an image-guided endoscopic biopsy device. Other image-guided devices/instruments may also be provided by the invention.

In some embodiments, an image-guided medical instrument according to the invention may include a handle, a body member, a treatment apparatus, an operating element, a transmission element, a sensor element, and/or other elements.

In one embodiment, the body member may include one or more elongated flexible elements or materials such as, for example, elongated tubing, wires, and/or other elements. In one embodiment, the body member may connect the handle to the treatment apparatus over or through the flexible elements comprising the body member. In some embodiments, the body member may also include an extended channel along its length such as, for example, the lumen of tubing, the lumen or channel of a hollow needle, or the lumen of another hollow flexible material.

In one embodiment, the body member may include or house one or more elements that transmit forces, energy, materials (e.g., solid, liquid, or gas materials) or other implements from the handle (or other part of the image-guided medical instrument) to the treatment apparatus. These elements may be referred to herein as "transmission elements." For example, transmission elements used in the invention may transmit extension/compression forces, rotational forces, electromagnetic energy, drugs or other solid, liquid, or gas materials, or other implements. In some embodiments, the transmission elements may include elements that can transmit mechanical forces such as, for example, wires, cables, tubes, or screw mechanisms, or other elements. In other embodiments, the transmission elements may include a shape memory alloy, a fluid (e.g., liquid or gas), an optical fiber, a wave guide for sound or electromagnetic energy, or other elements. In still other embodiments, the transmission elements may include electrical cables or electrical wires.

In some embodiments, the transmission elements may be contained within the extended channel/lumen of the body member. In one embodiment, the transmission elements may move independently of the body member. In some embodiments, the body member itself may act as a transmission element.

In some embodiments, the properties of the transmission element may be tuned to provide high pushability, high torque transmission, high kink resistance, low ductility, and/or other characteristics necessary for transmitting the intended energy or material along the transmission element.

As mentioned above, the image-guided medical instrument of the invention may include a treatment apparatus. In one embodiment, the treatment apparatus may include one or more movable parts such as, for example, jaws, a snare, a moving notch, a vibrating section, a steering mechanism, or other movable parts. In some embodiments, the treatment apparatus may include one or more non-movable parts such as, for example, an optical fiber tip, an electrode tip, a suction tube, or other non-movable parts.

In one embodiment, the treatment apparatus may be connected to the transmission element. The transmission element may transmit energy and/or material from the operating element or other part of the instrument to the treatment apparatus.

In some embodiments, the treatment apparatus may be actuated when a user triggers an operating element. In some embodiments, the operating element may include a trigger or other element on the handle. For example, the treatment apparatus may include a pair of biopsy jaws. In this example, the biopsy jaws may be opened and closed by actuating a movable trigger on the handle of the image-guided medical instrument. The movable trigger causes the transmission element to actuate the treatment apparatus. Other types operating elements may be used to actuate various types of treatment apparatuses.

The image-guided medical instrument of the invention may include at least one sensor element. In one embodiment, the sensor element may include an electromagnetic sensor element/position indicating element whose position and orientation may be tracked by an electromagnetic tracking device. Other types of tracking devices and sensor elements may be used such as, for example, inertial sensors, fiber optic position sensors, ultrasonic position sensors, global positions ("time of flight") sensors, or other devices or sensors.

In one embodiment, the sensor element may be located near the treatment apparatus along the body member. In other embodiments, the sensor element may be located elsewhere on the image-guided medical instrument. In still other embodiments, one or more sensor elements may be located near the treatment apparatus, while one or more other sensor elements may be located elsewhere on the image-guided medical instrument.

If the sensor element includes wires to receive or transmit signals, accommodation may be made to house these wires along the body member. For example, any wires necessary for the sensor element may be housed in the extended channel/lumen of the body member along with any electrical insulation, shielding, batteries, or other components.

In some embodiments, the transmission element may include a hollow tube (e.g., an "actuator tube"), in which lead-wires or other components of the sensing element can reside. Additional components may also be housed in or attached to a lumen of a hollow transmission element.

A tracking device associated with the sensor element may detect the relative position and/or orientation of the sensor element (and/or any object rigidly attached thereto). This relative position/orientation information may be used, as described herein, to guide the image-guided medical instrument through the anatomy of a patient for the purpose of performing a procedure.

The invention also provides an image-guided surgery system that can be used with the image-guided medical instruments described herein. In particular, the device and system of the invention are particularly appropriate for the manufacture of thin elongated instruments whose distal end includes a treatment apparatus and whose proximal end includes a handle. In order to perform a procedure accurately, it is advantageous to track the proximal end of the instrument using one or more sensor elements (such as, for example, those described herein) that do not otherwise alter the function or appearance of the instrument.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION

Figure 1:
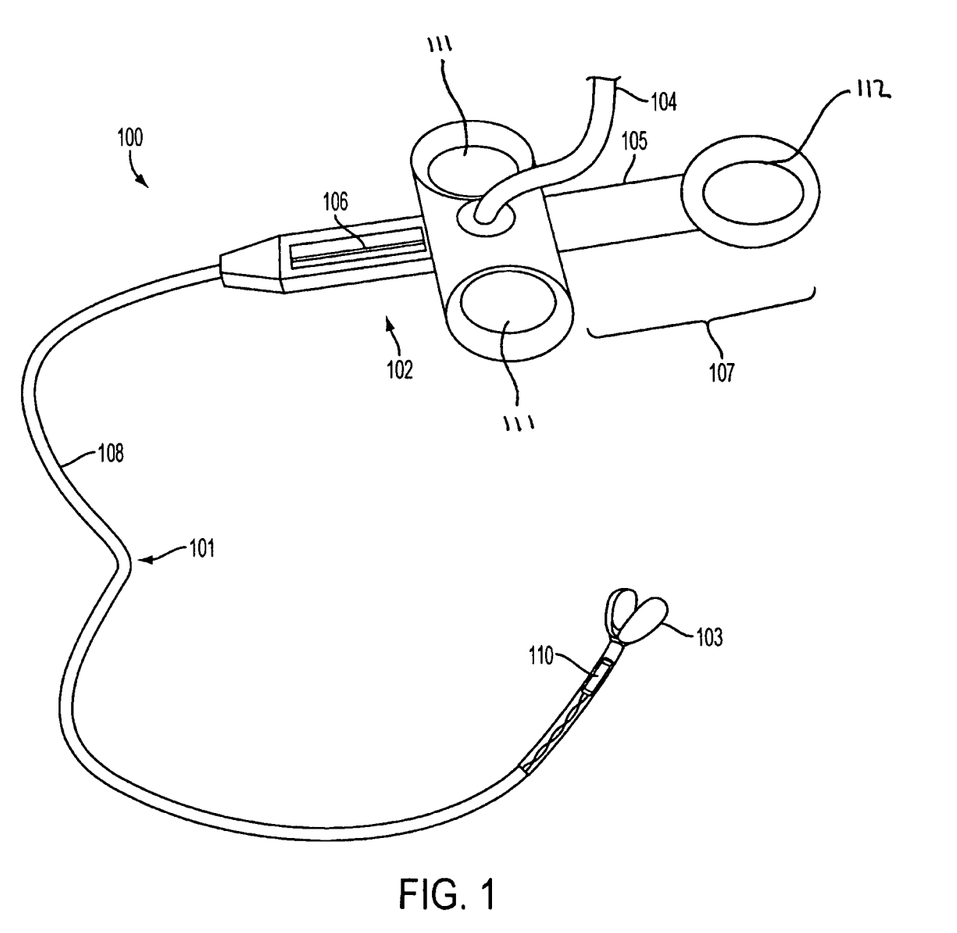
FIG. 1 illustrates an image-guided medical instrument, according to an embodiment of the invention.

In one embodiment, the invention provides an image-guided medical instrument, which can be used in minimally invasive surgery. FIG. 1 illustrates an image-guided medical instrument 100, according to an embodiment of the invention. In some embodiments, image-guided medical instrument 100 may include a body member 101, a handle 102, a treatment apparatus 103, an operating element 107, and/or other elements.

In one embodiment, body member 101 may include one or more elongated flexible elements or materials such as, for example, elongated tubing, wires, and/or other elements. For example, in one embodiment, body member 101 may include tubing 108. Body member 101 may also include coiled springs, insulating and/or protective jackets, braided elements, and/or other elements.

In one embodiment, body member 101 may include first and second ends and may connect handle 102 to treatment apparatus 103 over or through the flexible elements comprising body member 101.

Body member 101 may also include an extended channel along its length such as, for example, the lumen of tubing 108, the lumen of a hollow needle, or the lumen or channel within another hollow flexible element. The extended channel may house or contain other elements of instrument 100 and/or may act to transmit signals, forces, material, energy, and/or other implements either directly or indirectly from handle 102 or other element of instrument 100 to treatment apparatus 103.

In one embodiment, body member 101 may include or house one or more elements that transmit forces, energy, materials (e.g., solid, liquid, or gas materials) or other implements from handle 102 (or other part of instrument 100) to treatment apparatus 103. These elements may be referred to herein as "transmission elements." For example, transmission elements used in the invention may transmit extension/compression forces, rotational forces, electromagnetic energy, drugs or other solid, liquid, or gas materials, or other implements. In some embodiments, the transmission elements may include elements that can transmit mechanical forces such as, for example, wires (e.g., wire 106), cables, tubes, or screw mechanisms, or other elements. In other embodiments, the transmission elements may include a shape memory alloy, a fluid (e.g., liquid or gas), an optical fiber, a wave guide for sound or electromagnetic energy, or other elements. In still other embodiments, the transmission elements may include electrical cables or electrical wires. FIG. 1 illustrates wire 106 running though a portion of handle 102. Although not illustrated in FIG. 1, those having skill in the art will recognize that, in some embodiments, wire 106 (or other transmission element) may have first and second ends and may run from handle 102 through body member 101 to treatment apparatus 103.

In some embodiments, the transmission elements may be contained within the extended channel (e.g., a lumen of tubing 108) of body member 101. In one embodiment, the transmission elements may move independently of tubing 108 of body member 101. In some embodiments, tubing 108 of body member 101 itself may act as a transmission element and may include electrical functional or electrically activated elements (e.g., coils, piezoelectric devices, motors, thermal ablative devices, sampling vents or ports, or other electrical devices), mechanical elements (e.g., steering wires, springs, shape-set wires, tensile members, or other mechanical elements), functional elements (e.g., sliding cannulae or other functional elements), elements that change the mechanical, chemical, biological, and/or electrical characteristics of body section 101, additional sensors (e.g., additional position indicating sensor elements, temperature sensors, pressure sensors, or other sensors), and/or other elements.

In one embodiment, treatment apparatus 103 may include one or more movable parts such as, for example, jaws, a snare, a moving notch, a vibrating section, a steering mechanism, or other movable parts. In some embodiments, treatment apparatus 103 may include one or more non-movable parts such as, for example, an optical fiber tip, an electrode tip, a suction tube, or other non-movable parts. FIG. 1 illustrates a pair of movable jaws as treatment apparatus 103. Those having ordinary skill in the art will recognize that a variety of elements including, but not limited to, the aforementioned elements may be used as treatment apparatus 103. For example, treatment apparatus 103 may include a biopsy element (e.g., biopsy jaws, a biopsy gun, a biopsy notch, endoscopic biopsy forceps, or other biopsy element), a polypectomy snare, a cytology brush, a biliary guidewire, a sphincterotome, an Endoscopic Retrograde Cholangio-Pancreatography (ERCP) catheter, a stone retrieval balloon, a stent, a lithotripsy basket, a grasper, a basket, rat-tooth forceps, alligator forceps, a sclerotherapy/injection needle, a bipolar coagulation probe, a dilation balloon, a radiofrequency ablation device, a microwave ablation device, embolic delivery device, brachytherapy device, a cryotherapy probe, and/or other treatment apparatus.

In some embodiments, treatment apparatus 103 may be actuated when a user triggers operating element 107. In some embodiments, operating element 107 may include a trigger in handle 102, which may further include an electrical switch or contact. In one embodiment, operating element 107 may include a movable part 105 that comprises all or part of operating element 107. For example, as illustrated in FIG. 1, treatment apparatus 103 includes a pair of biopsy jaws. In this example, the biopsy jaws may be opened and closed by actuating movable part 105. Movable part 105 may be operated by a thumb piece 112 of operating element 107, through which an operator's thumb may be inserted. Finger holes 111 may also be included on handle 102, such that an operator may place one or more fingers in each finger hole 111 and slidably actuate operating element 107 with his or her thumb using thumb piece 112. This slidable actuation of operating element 107 causes wire 106 to move accordingly in body member 101, which causes the jaws of treatment apparatus 103 to open and close. Those having skill in the art will realize that the embodiment illustrated in FIG. 1 is exemplary only and that other embodiments may be used.

In one embodiment, operating element 107 may actuate an electric motor, pump, microwave generator, or other electrical or mechanical device that may be partly or fully contained in handle 102. This electrical/mechanical device may cause forces, energy, material, or other implements to be transmitted via the transmission element of body member 101 and actuate treatment apparatus 103.

In one example, operating element 107 may be purely mechanical and may actuate treatment apparatus 103 directly via transmission elements with or without the assistance of springs, pulleys, hinges, rods, cables, wires, screws or other mechanical devices. In another example, operating element 107 may be a fluidic element such as a valve and may control the passage of fluids (e.g., liquids or gasses) through transmission section 101 to operating section 103.

Image-guided medical instrument 100 may include at least one sensor element 110. In one embodiment, sensor element 110 may include an electromagnetic sensor element/position indicating element whose position and orientation may be tracked by an electromagnetic tracking device. Other types of tracking devices and sensor elements may be used such as, for example, optical tracking devices, fiber optic devices, ultrasonic devices, global positioning ("time of flight") devices, inertial sensors, or other tracking devices and sensor elements.

In one embodiment, sensor element 110 may be located near treatment section 103, along body member 101. In other embodiments, sensor element 110 may be located elsewhere on medical instrument 100. If sensor element 110 includes wires to receive or transmit signals, accommodation may be made to house these wires along body member 101. For example, the wires necessary for sensor element 110 may be housed in the extended channel of body member 101 (e.g., in the lumen of tubing 108).

As mentioned above, one embodiment of the invention includes treatment apparatus 103 that is connected to a transmission element and/or body member 101. The transmission element may, in some embodiments, transmit mechanical motion from operating element 107 to treatment apparatus 103. In these embodiments, the transmission element may include a hollow tube (e.g., an "actuator tube"), in which lead-wires from sensing element 110 can reside. Additional components may also be housed in or attached to a lumen of a hollow transmission element.

Figure 2:
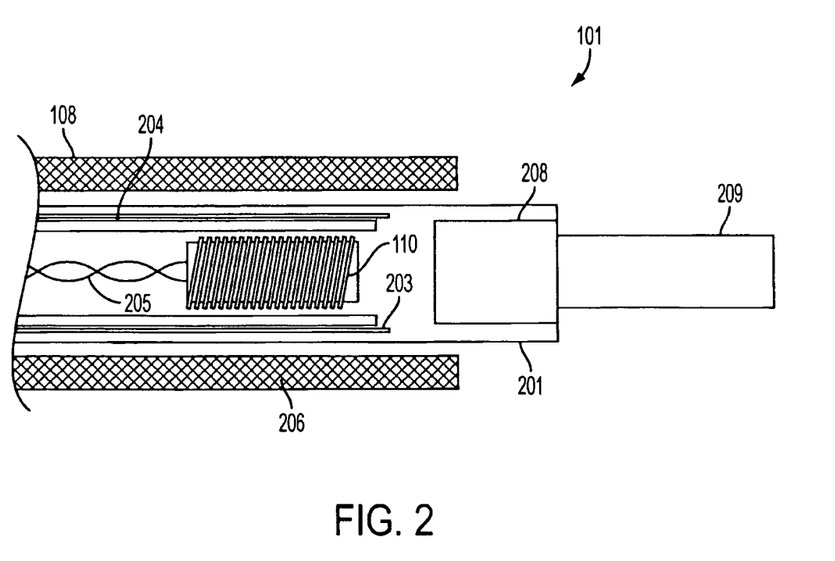
FIG. 2 illustrates the end of a body member having a sensor element, according to an embodiment of the invention.

FIG. 2 illustrates a cross-section of a portion of body member 101 of image-guided medical instrument 100. Body member 101 may include tubing 108 (e.g., a jacket tube), which may be used to house a transmission element in the form of an actuator tube 201. In one embodiment, tubing 108 may include braid-reinforced or other structurally stabilized metal or plastic, or a metal spring coil that may contain additional layers or coatings depending on the use. In some embodiments, tubing 108 also may assist any actuating elements (e.g., actuator tube 201) to actuate a treatment apparatus (not illustrated in FIG. 2), thereby causing the treatment apparatus to move or operate (e.g. ablate, take tissue samples, or otherwise operate).

As mentioned above, actuator tube 201 may serve as a transmission element and thus may perform the function of transmitting forces, energy, material, or other implements from an operating element 107 (not illustrated in FIG. 2) or other element of instrument 100 to a treatment apparatus. In other embodiments, the transmission element may include a solid wire, a wire cable, or other element.

In one embodiment, actuator tube 201 (or other part of transmission section 101) may be instrumented with at least one sensor element 110. In one embodiment, sensor element 110 may be capable of providing certain parameters such as its location and/or orientation relative to a companion tracking device (or the location/orientation of any object that is rigidly attached to sensor element 110). This relative position/orientation information may be used, as described herein, to guide image-guided medical instrument 100 through the anatomy of a patient for the purpose of performing a procedure.

In one embodiment, sensor element 110 may be secured within a lumen of actuator tube 201 and may contain electrical insulation 203, electrical shielding 204, lead-wires 205, any necessary batteries, and/or other elements. In some embodiments, actuator tube 201 may include a conventional tube such as, for example, a hypodermic tube, into which sensor element 110, insulation 203, shielding 204, lead-wires 205 and/or other elements have been fixed. In another embodiment, actuator tube 201 may include a hollow multifilar wire rope which allows for the placement of sensor element 110 and/or any elements within the core of the wire rope.

In one embodiment, lead-wires 205 (signal carrying wires) may be threaded back through the lumen/hollow core of actuator tube 201 to the handle (e.g., handle 102) of instrument 100. In an alternate embodiment, lead-wires 205 may be incorporated into the wall of a tube (e.g., tubing 108, actuator tube 201, or other tube) using, for example, the conductor embedded Polyimide tubing manufactured by the Phelps Dodge Company. In one embodiment, lead-wires 205 may exit medical instrument 100 at its handle (e.g., see item 104 of FIG. 1).

The properties of actuator tube 201 or other transmission element may be tuned to provide high pushability, high torque transmission, high kink resistance, low ductility, and/or other characteristics necessary depending on the intended force, energy, material or other implement to be transmitted.

In some embodiments, sensor element 110 may be connected to external devices such as, for example, sensor element 110's companion tracking device, one or more computer-implemented systems, a control unit, or other devices. Sensor element 110 may be connected to these devices using either a wired or wireless configuration. In some embodiments, a wireless tracking device/sensor element apparatus may be powered externally or by using batteries.

In other embodiments, lead-wires 205 may be incorporated into or attached to another part of body member 101. For example, a solid actuator wire may be used in place of or in addition to actuator tube 201. In this example, a conductor embedded tube or lead-wires 205 themselves can be overlaid over top of an actuator wire. In still another embodiment, a notch carved along the length of the actuator wire can be used to house lead-wires 205.

In one embodiment, sensor element 110 may be bonded to an actuation cable and lead-wires 205 may be connected to the cable strands or wound with them, and signals conducted down the actuation cable. In yet another embodiment, a hollow sensor element 110 may be used and an actuation wire may pass through the center of the hollow sensor element 110. In this embodiment, lead-wires 205 may run alongside the actuation wire or can be routed through the center of a hollow actuation wire. In this case, hollow sensor element 110 may be bonded to an external jacket (e.g., the jacket tube comprising tubing 108), and an actuation wire may be freely slidable through the center of hollow sensor element 110.

In yet another embodiment, a force transmission element other than actuator tube 201 may include a solid wire that has been machined to contain a groove along its length for lead wires 205 to run, and a space integrated into the wire near the distal end for sensor element 110.

Referring back to FIG. 2, at the distal tip of actuator tube 201, additional components such as, for example, items 208 and/or 209 may be welded or otherwise attached to, or formed from, actuator tube 201 or other transmission element. Items 208 and/or 209 may enable a hollow actuator tube 201 to be efficiently adapted for attachment to a treatment apparatus without having to significantly alter existing or pre-manufactured treatment apparatus components (e.g., standard biopsy jaws or other standard or pre-manufactured components).

Figure 3A:
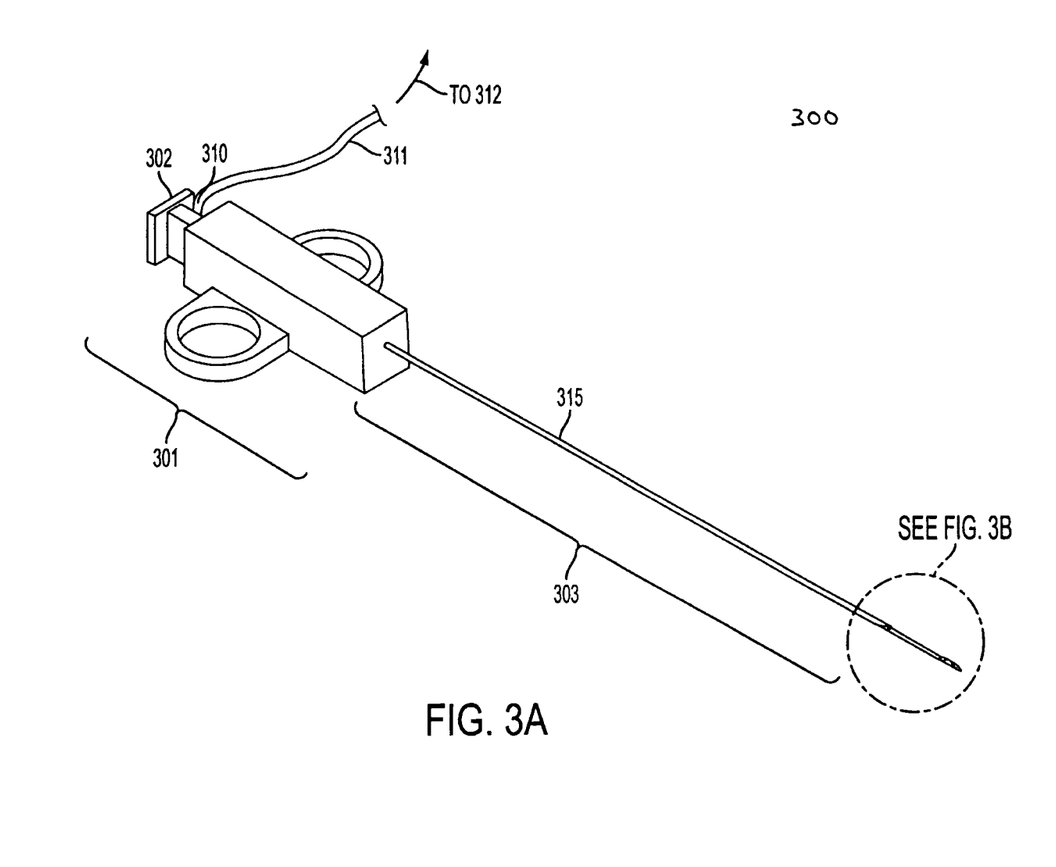
FIG. 3A illustrates an image-guided medical instrument, according to an embodiment of the invention.
Figure 3B:
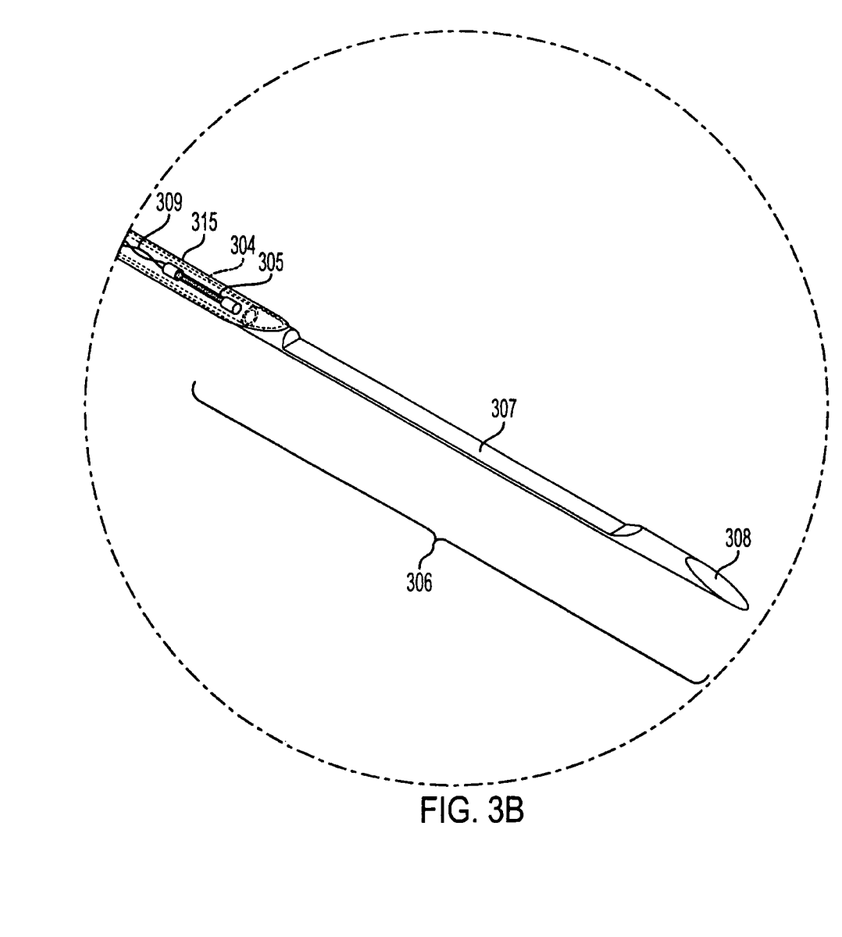
FIG. 3B illustrates the tip of an image-guided medical instrument, according to an embodiment of the invention.

FIGS. 3A and 3B illustrate an image-guided medical instrument 300 according to an embodiment of the invention. Instrument 300 illustrates a biopsy device. However, those of skill in the art will realize that medical instruments having other functions may be similarly utilized as image guided medical instrument 300. Image-guided medical instrument 300 includes a handle 301. In one embodiment, handle 301 may include an operating element 302, which may enable actuation of a treatment apparatus 306.

Image-guided medical instrument 300 also includes an elongated body member 303. In one embodiment, body member 303 may include a hollow cannula 315. In some embodiments, hollow cannula 315 may serve as a protective jacket tube and/or may enable functionality of treatment apparatus 306, as described below. FIG. 3B illustrates a cross-section of a portion body member 303 that is attached to treatment apparatus 306. In one embodiment, body member 303 may include a transmission element 304. Transmission element 304 may include a hollow tube that is freely slideable within the jacket tube provided by hollow cannula 315.

A sensor element 305 may be fixed within transmission element 304 near its end or may be housed in another part of instrument 300. Lead-wires 309 may extend from sensor element 305 back through transmission element 304 to handle 301 where lead-wires 309 can exit at a location 310 to an external cable 311 and ultimately to a device 312 that can process the signal from sensor element 305 (e.g., a tracking device, a computer-implemented processing system, and/or a control unit).

In one embodiment, instrument 300 may also include a treatment apparatus 306. Treatment apparatus 306 may include a section of wire or other material that is welded or otherwise fixed to transmission element 304. Treatment apparatus 306 may be manufactured in the manner of existing biopsy devices so that it includes a notched section 307 and a point 308. Point 308 may be beveled or come to a sharp point.

The actuation of device 300 may cause hollow cannula 303 to slide forward (e.g., to the right as illustrated in FIGS. 3A and 3B) over notched section 307 of treatment apparatus 306, trapping a sample of tissue in the notch of notched section 307. As such, in this embodiment, transmission element 304, does not directly transmit forces that actuate treatment apparatus 306, as much as it serves as a guide/support for hollow cannula 315.

Figures 4A, 4B:
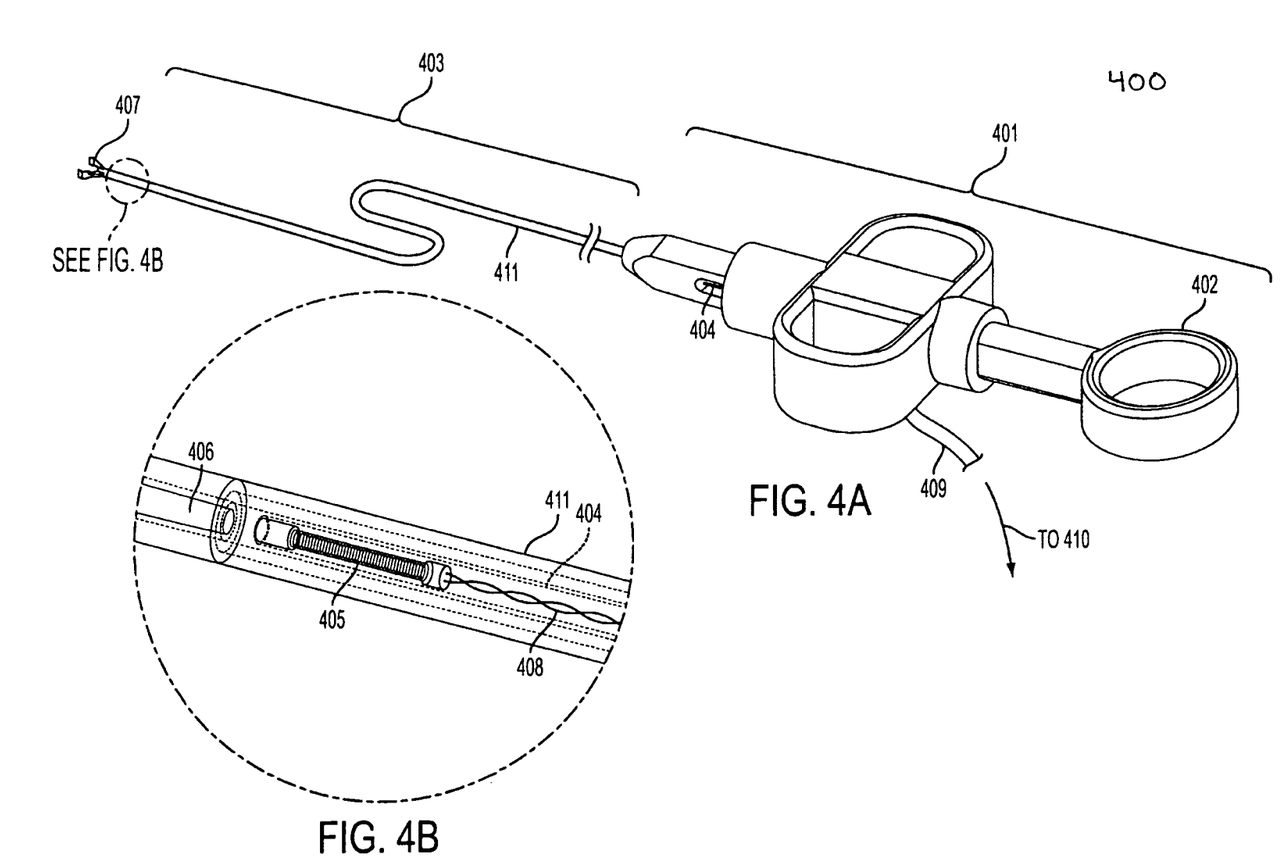
FIG. 4A illustrates an image-guided medical instrument, according to an embodiment of the invention.
FIG. 4B illustrates a body member of an image-guided medical instrument, according to an embodiment of the invention.
Figure 4C:
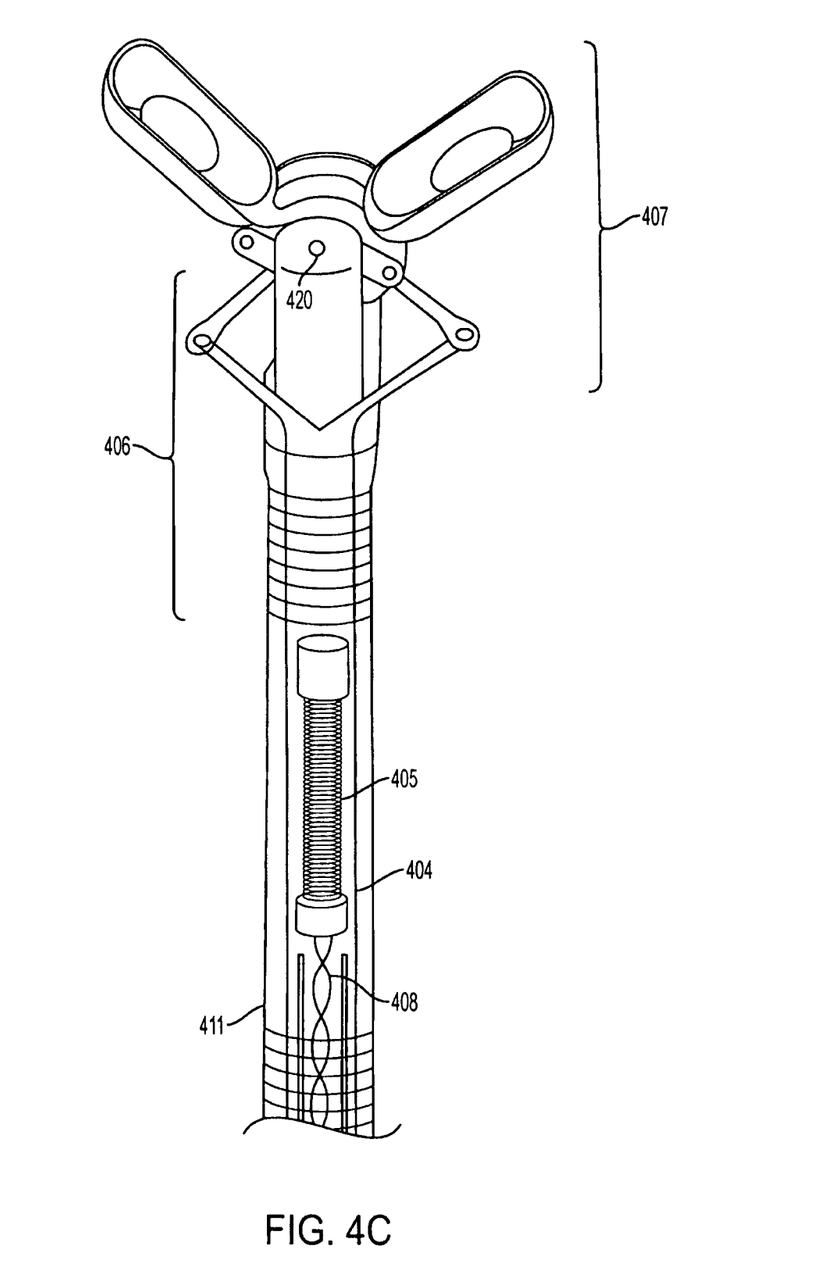
FIG. 4C illustrates the tip of an image-guided medical instrument, according to an embodiment of the invention.

FIGS. 4A, 4B and 4C illustrate an image-guided medical instrument 400 according to an embodiment of the invention. As illustrated, instrument 400 is an endoscopic biopsy gasper. However, instrument 400 is exemplary only. Those having skill in the art will recognize that instruments having different treatment apparatuses may be used.

As illustrated, instrument 400 includes a handle 401, a body member 403, and a treatment apparatus 407. Handle 401 includes an operating element 402 that enables actuation of treatment apparatus 407.

Body member 403 may include flexible hollow tube 411, which may serve as a protective jacket tube. Body member 403 may also include a transmission element 404. Transmission element 404 may include a flexible hollow tube that is housed within and is freely slideable within jacket tube 411.

A sensor element 405 may be fixed within the lumen of transmission element 404 near its distal end. A tip section 406 of wire or other material may be welded or otherwise fixed to transmission element 404. Tip section 406 may be manufactured so that it can connect an otherwise standardized treatment section 407 (in this embodiment, a pair of biopsy jaws usable with traditional medical instruments) to transmission section 403, thereby saving the effort of redesigning special jaws.

Lead-wires 408 may extend from sensor element 405 back through transmission element 404 or other part of transmission section 403, to handle 401. Lead-wires 408 then exit handle 401 to an external cable 409 and may ultimately connect to a device 410 that can process the signal from sensor element 405 (e.g., a tracking device or computer-implemented processing device).

FIG. 4C illustrates sensor element 405 and treatment apparatus 407 in detail. As illustrated, jacket tube 411 is connected to the hinge mechanism 420 via tip portion 406. In the region at the distal end of sensor element 405, hollow force transmission element 404 is attached to a standard mechanism for treatment apparatus 407 (in this embodiment, the pair of biopsy jaws).

Figure 5:
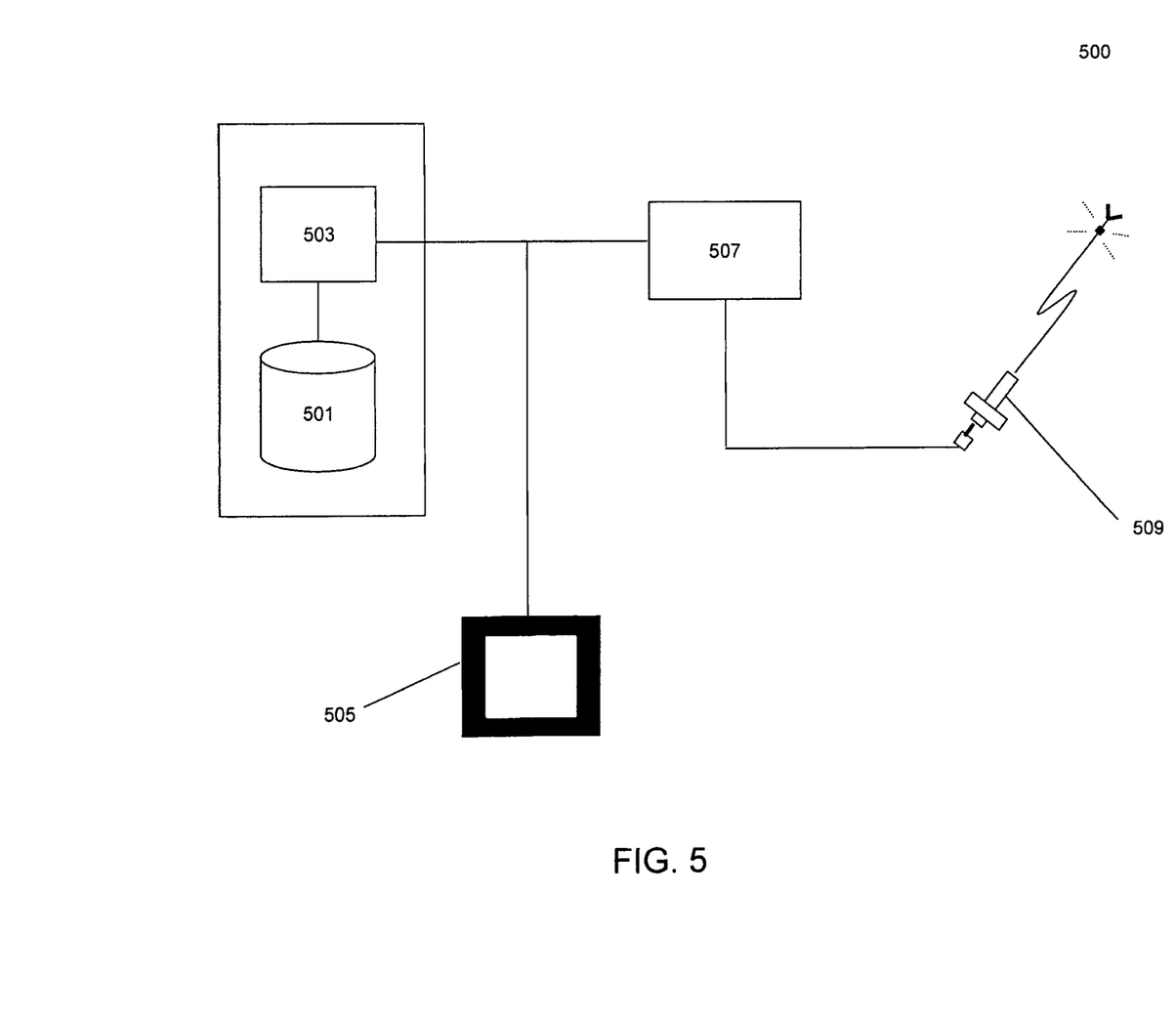
FIG. 5 illustrates a system for performing a medical procedure using an image-guided medical instrument, according to an embodiment of the invention.

FIG. 5 illustrates an image-guided surgery system 500 according to an embodiment of the invention that can be used with the image-guided medical instruments provided by the invention (e.g., instruments, 100, 300, 400, or other instruments). System 500 may include a memory device 501, a processing unit 503, a display device 505, a position sensing device 507, an image-guided medical instrument 509, and/or other elements.

In one embodiment, system 500 may include memory device 501. Memory device 501 may include a hard-drive, flash memory, or other computer-implemented memory that receives and stores image data obtained from an imaging modality such as, for example, an x-ray device, a magnetic resonance imaging (MRI) device, a positron emission tomography (PET) device, a fluoroscopic device, and ultrasound device, or other imaging modality. Memory device 500 may also receive and store position and/or orientation data related to a sensor element and may store other data for use with the systems and methods of the invention.

In one embodiment, system 500 may also include processing unit 503. Processing unit may include one or more computer-implemented microprocessors and/or computer systems including one or more microprocessors. Processing unit 503 may processes and/or manipulate image data related to a patient's anatomy, position and/or orientation data regarding a sensor element, and/or other data for use in image guided surgery and the systems and methods of the invention.

System 500 may also include display device 505. Display device 500 may include a computer monitor (e.g., cathode ray tube, LCD screen, or other monitor) that produces one or more images illustrating image data, position data, combinations thereof, or other data to a user (e.g., a surgeon).

System 500 may also include a tracking device 507 that can detect the location and orientation of a sensor element/position indicating element (e.g., sensor element 110, 305, 405) in image-guided medical instrument 509. In one embodiment, tracking device 507 may include an electromagnetic tracking device that can detect the position and/or orientation of one or more electromagnetic sensor elements/position indicating elements. Other types of tracking devices and sensor elements may be used such as, for example, optical tracking devices/sensor elements, fiber optic devices, ultrasonic devices, global positioning ("time of flight") devices, inertial sensor devices, or other tracking devices and sensor elements.

In some embodiments, system 500 may also include one or more software modules enabling the features and functions of the invention. Those having skill in the art will appreciate that the invention described herein may work with various system configurations. Accordingly, more or less of the aforementioned system components may be used and/or combined in various embodiments. It should also be understood that software modules used to accomplish the functionalities described herein may be maintained on one or more of the components of system recited herein, as necessary, including those within individual medical tools or devices. In other embodiments, as would be appreciated, the functionalities described herein may be implemented in various combinations of hardware and/or firmware, in addition to, or instead of, software.

Figure 6:
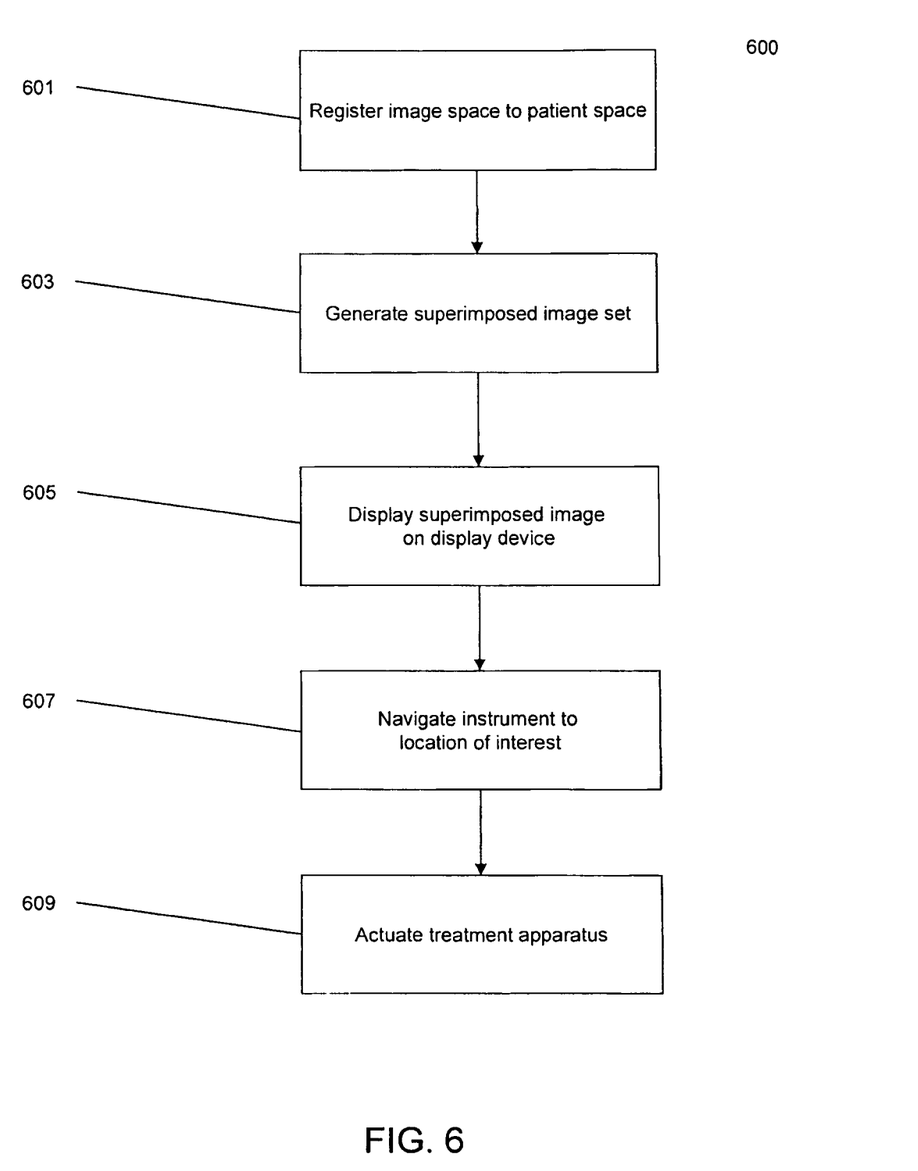
FIG. 6 illustrates a process for performing a medical procedure using an image-guided medical instrument, according to an embodiment of the invention.

FIG. 6 illustrates a process 600 for using an image guided medical instrument (e.g., instrument 100, 300, 400) with an image-guided surgery system (e.g., system 500) for performing image guided surgery or other image-guided procedure/intervention. Process 600 includes an operation 601, wherein images of a patient's anatomy obtained using an imaging modality are registered to a patient space according to one or more methods known in the art. For information regarding registration, image-guided surgery, or other information related to the invention, see U.S. patent application Ser. No. 11/059,336 (U.S. Patent Publication No. 2005/0182319), entitled "Method and Apparatus for Registration, Verification, and Referencing of Internal Organs," which is hereby incorporated by reference herein in its entirety.

In an operation 603, a graphic representation of part or all of the image-guided medical instrument is generated and superimposed on one or more images (e.g., preoperative images) of the patient anatomy. In an operation 605, these superimposed images are displayed on the display device. In some embodiments, the position of the sensor element may be extrapolated to the tip of the image-guided medical instrument, to the center of the treatment apparatus (e.g., to the middle of the jaws) or some other suitable location that is convenient in the context of the intervention (e.g., the location most relevant to guiding the treatment apparatus to a location of interest) using the known relationship between the treatment apparatus (or other location) and the sensor element. In an operation 607, the image-guided medical instrument can be navigated to a treatment location, sampling location, or location of interest in the anatomy of a patient using the superimposed representation of the instrument on the one or more images of the patient's anatomy.

In an operation 609, when the display device shows that the treatment apparatus of the medical instrument is in a treatment or sampling location, an operating element (e.g., operating elements 107, 302, 402) can be actuated to actuate a treatment apparatus (e.g., treatment apparatuses 103, 306, 407) via a transmission element (e.g., transmission elements 201, 304, 404) and a sample may be taken or therapy may be delivered.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. An image-guided medical instrument that utilizes a tracking device to track a location of at least a portion of the instrument on at least one image of an anatomy, the image-guided medical instrument comprising:
   a handle that includes an operating element;
   a treatment apparatus;
   an elongated flexible body member comprising a first end of the body member coupled to the handle, a second end of the body member coupled to the treatment apparatus, and a first lumen; and
   a transmission element configured to actuate the treatment apparatus in response to actuation of the operating element, wherein the transmission element is disposed inside the first lumen and comprises a first end of the transmission element coupled to the operating element, a second end of the transmission element coupled to the treatment apparatus, and a second lumen including at feast one sensor element,
   wherein the at least one sensor element is located at the second end of the body member adjacent to the treatment apparatus, wherein the at least one sensor element, disposed inside the second lumen, is configured to obtain position information regarding a position of the at least one sensor element, and wherein the location of the treatment apparatus on the at least one image of the anatomy is able to be determined using the position information of the at least one sensor element.

2. The image-guided medical instrument of claim 1, wherein the body member comprises a hollow tube.

3. The image-guided medical instrument of claim 1, wherein the transmission element comprises a torqued cable bundle comprising a hollow wire-rope manufactured as a bundle of twisted filaments, wherein the hollow portion forms the second lumen.

4. The image-guided medical instrument of claim 1, wherein the body member comprises a hollow helical spring winding.

5. The image-guided medical instrument of claim 1, wherein the transmission element comprises a wire, and wherein the treatment apparatus is actuated when force is transmitted along the transmission element.

6. The image-guided medical instrument of claim 1, wherein the transmission element mechanically actuates the treatment apparatus.

7. The image-guided medical instrument of claim 1, wherein the transmission element includes one or more electrical conductors that serve as signal pathways for the at least one sensor element.

8. The image-guided instrument of claim 1, wherein the transmission element includes one or more electrical conductors provide electrical energy to the treatment apparatus.

9. The image-guided instrument of claim 1, wherein the transmission element includes one of a waveguide that transmits microwave energy to the treatment apparatus or an optical fiber that transmits optical energy to the treatment apparatus.

10. The image-guided medical instrument of claim 1, wherein the position information includes information regarding the orientation of the at least one sensor element.

11. The image-guided medical instrument of claim 1, wherein the treatment apparatus comprises a biopsy device.

12. The image-guided medical instrument of claim 1, wherein the treatment apparatus comprises one of a biopsy element, a biopsy notch, endoscopic biopsy forceps, a polypectomy snare, a cytology brush, a biliary guidewire, a sphincterotome, an Endoscopic Retrograde Cholangio-Pancreatography (ERCP) catheter, a stone retrieval balloon, a stent, a lithotripsy basket, a grasper, a basket, rat-tooth forceps, alligator forceps, a sclerotherapy/injection needle, a bipolar coagulation probe, a dilation balloon, a radiofrequency ablation device, a microwave ablation device, embolic delivery device, brachytherapy device, or a cryotherapy probe.

13. The image-guided medical instrument of claim 1, wherein the tracking device includes an electromagnetic tracking device and the sensor element includes an electromagnetic position sensor.

14. The image-guided medical instrument of claim 1, wherein sensor element includes one of an inertial sensor, an ultrasonic position sensor, or a fiber optic position sensor.

15. The image-guided medical instrument of claim 1, wherein the transmission element facilitates receiving electromagnetic energy transmitted from the second end of the body member.

16. A method for facilitating performance of a procedure on a location of interest within a portion of an anatomy of a patient using at least one image of the anatomy of the patient, a tracking device, and an image-guided medical instrument, wherein the image-guided medical instrument includes an operating element, a transmission element comprising a lumen, a treatment apparatus, and at least one sensor element that is trackable by the tracking device, wherein the at least one sensor element is located in the lumen at an end adjacent to the treatment apparatus, the method comprising:
   receiving the at least one image of the anatomy of the patient;
   receiving position information regarding the position of the at least one sensor, wherein the at least one sensor is disposed inside the lumen of the transmission element;
   registering the position information to the at least one image of the anatomy of the patient;
   displaying the location of the treatment apparatus on at least one image of the anatomy of the patient, wherein navigation of the treatment apparatus to the location of interest is facilitated using the displayed location of the treatment member; and
   actuating, by the transmission element, the treatment apparatus in response to actuation of the operating element, wherein performance of the procedure on the location of interest is based at least in part on the actuation of the treatment apparatus.

* * * * *